United States Patent [19]

Baasner et al.

[11] 4,429,154
[45] Jan. 31, 1984

[54] FLUORINATED AZOMETHINE COMPOUNDS

[75] Inventors: Bernd Baasner, Leverkusen; Erich Klauke, Odenthal; Hermann Hagemann, Cologne; Engelbert Kühle, Bergisch-Gladbach, all of Fed. Rep. of Germany

[73] Assignee: Bayer Aktiengesellschaft, Leverkusen, Fed. Rep. of Germany

[21] Appl. No.: 381,132

[22] Filed: May 24, 1982

Related U.S. Application Data

[63] Continuation of Ser. No. 254,718, Apr. 16, 1981.

[30] Foreign Application Priority Data

May 10, 1980 [DE] Fed. Rep. of Germany ....... 3018020

[51] Int. Cl.³ .......................................... C07C 119/08
[52] U.S. Cl. .................................... 564/278; 564/209; 71/88; 71/92; 71/94; 71/95; 71/100; 71/118
[58] Field of Search ........................................ 564/278

[56] References Cited

PUBLICATIONS

Hine, Jack et al., J. of Org. Chemistry, (1970), vol. 35, pp. 340–344.

*Primary Examiner*—Natalie Trousof
*Assistant Examiner*—L. Hendriksen
*Attorney, Agent, or Firm*—Felfe & Lynch

[57] ABSTRACT

New fluorinated azomethines of the general formula

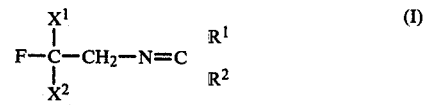

in which
$X^1$ represents hydrogen, fluorine or chlorine,
$X^2$ represents hydrogen, fluorine or chlorine,
$R^1$ represents hydrogen or alkyl and
$R^2$ represents hydrogen or alkyl, a process for their preparation and their use as intermediate products.

7 Claims, No Drawings

FLUORINATED AZOMETHINE COMPOUNDS

This is a continuation application of Ser. No. 254,718 filed Apr. 16, 1981.

This invention relates to certain novel fluorinated azomethine compounds. Further, the invention relates to a process for the preparation for such compounds and in additional aspects, to the use of such compounds as intermediates for the synthesis of herbicide antagonists.

It is known that certain azomethine compounds can be prepared by reacting amines with carbonyl compounds (see, e.g., J.Amer.Chem.Soc. 66, 82 (1944)). However, corresponding fluorinated azomethine compounds have not hitherto been described.

It has also already been disclosed that N,N-di-n-propyldichloroacetamide is suitable as an antidote ("safener") for improving the tolerance of crop plants to herbicidally active thiolcarbamates or acetanilides (see DE-OS (German Published Specification) 2,218,097). However, the activity of this substance as an antidote is not always completely satisfactory.

By "antidotes" there are to be understood, in the present connection, substances which are capable of specifically antagonising harmful effects of herbicides on crop plants, that is to say of protecting the crop plants without thereby noticeably influencing the herbicidal action on the weeds to be combated.

The present invention now provides, as new compounds, the fluorinated azomethines of the general formula

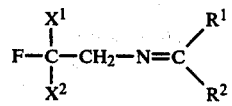

in which
X$^1$ represents hydrogen, fluorine or chlorine,
X$^2$ represents hydrogen, fluorine or chlorine,
R$^1$ represents hydrogen or alkyl and
R$^2$ represents hydrogen or alkyl.

The invention also provides a process for the preparation of a fluorinated azomethine of the formula (I), in which a fluorinated amine of the general formula

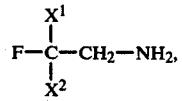

in which
X$^1$ and X$^2$ have the abovementioned meanings,
is reacted with a carbonyl compound of the general formula

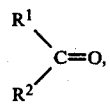

in which
R$^1$ and R$^2$ have the abovementioned meanings,
if appropriate in the presence of a diluent.

It has also been found that the fluorinated azomethines of the formula (I) can be used as intermediate products for the preparation of fluorinated halogenoacetamides, which have an antagonistic action on herbicidally active thiolcarbamates and acetanilides. Surprisingly, the fluorinated halogenoacetamides, which can be prepared from the fluorinated azomethines of the formula (I) by hydrogenation, and subsequent reaction of the resulting fluorinated amines with halogenoacetic acid chlorides, are more suitable for increasing the tolerance of crop plants to herbicidally active thiolcarbamates or acetanilides than N,N-di-n-propyl-dichloroacetamide, which is known from the state of the art and is an active compound with a high activity and the same type of action. The substances according to the invention thus represent, as intermediate products for the synthesis of antidotes, a valuable enrichment of the art.

The formula (I) provides a general definition of the fluorinated azomethines according to the invention. Preferably in this formula,
X$^1$ represents hydrogen, fluorine or chlorine,
X$^2$ represents hydrogen, fluorine or chlorine,
R$^1$ represents hydrogen or straight-chain or branched alkyl with 1 to 6 (especially 1 to 4) carbon atoms, and
R$^2$ represents hydrogen or straight-chain or branched alkyl with 1 to 6 (especially 1 to 4) carbon atoms.

Particularly preferred compounds of the formula (I) are those in which X$^1$ represents hydrogen, fluorine or chlorine, X$^2$ represents hydrogen, fluorine or chlorine, R$^1$ represents hydrogen, methyl, ethyl, n-propyl, isopropyl or n-butyl and R$^2$ represents hydrogen, methyl or ethyl.

If 2,2-difluoroethylamine and acetaldehyde are used as starting materials, the course of the process according to the invention can be represented by the following equation:

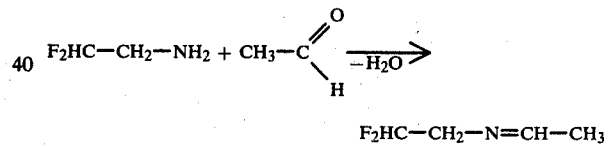

The formula (II) provides a general definition of the fluorinated amines required as starting materials in the process according to the invention. In this formula, X$^1$ and X$^2$ preferably have those meanings which have already been mentioned as preferred for these radicals in connection with the description of the substances of the formula (I).

The fluorinated amines of the formula (II) are known, or they can be prepared by processes which are known in principle (see J. Org. Chem. 24, (1959), 1,256–1,259).

The formula (III) provides a general definition of the carbonyl compounds also required as starting materials in the process according to the invention. In this formula, R$^1$ and R$^2$ preferably represent those radicals which have already been mentioned as preferred for R$^1$ and R$^2$ in connection with the description of the substances of the formula (I).

Specific examples of carbonyl compounds of the formula (III) which may be mentioned are: formaldehyde, acetaldehyde, propionaldehyde, 1-methyl-propionaldehyde, butyraldehyde, acetone and diethyl ketone.

The carbonyl compounds of the formula (III) are known.

If appropriate, the reaction in the process according to the invention is carried out in the presence of a diluent. Possible diluents are inert organic solvents. Preferred solvents are optionally halogenated aliphatic and cycloaliphatic hydrocarbons, such as pentane, hexane, cyclohexane, chloroform and carbon tetrachloride; optionally halogenated aromatic hydrocarbons, such as benzene, xylene, toluene and chlorobenzene; and ethers, such as diethyl ether, tetrahydrofuran and dioxan.

The reaction temperatures can be varied within a certain range in the process according to the invention. In general, the reaction is carried out at a temperature between −20° C. and +60° C., preferably between 0° C. and +40° C.

In carrying out the process according to the invention, 1 to 1.2 moles of carbonyl compound of the formula (III) are generally employed per mole of fluorinated amine of the formula (II). The mixture is worked up by customary methods. In general, a procedure is followed in which, when the reaction has ended, solid alkali metal hydroxide, preferably sodium hydroxide or potassium hydroxide, is added and the organic phase which subsequently separates out is then separated off, dried and distilled.

The fluorinated azomethines of the formula (I) according to the invention are suitable as intermediate products for the synthesis of fluorinated halogenoacetamides, which have an antagonistic action on certain herbicidally active thiolcarbamates and acetanilides. The fluorinated halogenoacetamides in question are characterized by the general formula

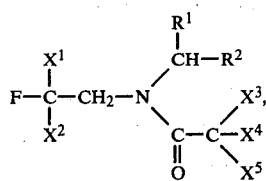
(IV)

in which
X$^1$, X$^2$, R$^1$ and R$^2$ have the abovementioned meaning,
X$^3$ represents hydrogen, fluorine or chlorine,
X$^4$ represents hydrogen, fluorine or chlorine and
X$^5$ represents fluorine or chlorine.

A fluorinated halogenoacetamide of the formula (IV) can be prepared by hydrogenating a fluorinated azomethine of the general formula

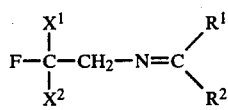
(I)

in which
X$^1$, X$^2$, R$^1$ and R$^2$ have the abovementioned meanings,
with hydrogen under a pressure of 3 to 15 bars, in the presence of a catalyst, such as platinum-on-charcoal, palladium-on-charcoal or Raney nickel, and in the presence of a diluent, for example an alcohol, such as methanol or ethanol, or an ether, such as dioxan, at a temperature between 0° C. and 60° C., preferably between 10° C. and 50° C., and then reacting the resulting fluorinated amine of the general formula

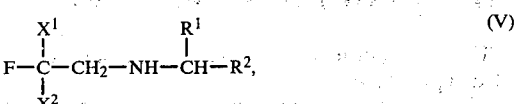
(V)

in which
X$^1$, X$^2$, R$^1$ and R$^2$ have the abovementioned meanings,
with a halogenoacetic acid chloride of the general formula

(VI)

in which
X$^3$, X$^4$ and X$^5$ have the abovementioned meanings, if appropriate in the presence of an acid-binding agent, such as triethylamine, and if appropriate in the presence of a diluent, such as toluene, at a temperature between 0° C. and 80° C.

Thus, for example, dichloroacetic acid N-(2,2,2-trifluoroethyl)-N-ethyl-amide of the formula

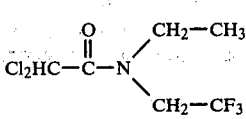

can be prepared by hydrogenating ethylidene-2,2,2-trifluoroethylamine in a first stage, under a hydrogen pressure of 10 bars in the presence of ethanol, and in the presence of platinum-on-charcoal, as the catalyst, and then reacting the resulting N-(2,2,2-trifluoroethyl)-N-ethylamine, in a second stage, with dichloroacetyl chloride in the presence of triethylamine as the acid-binding agent and in the presence of toluene as the diluent. This synthesis can be represented by equations as follows:

1st stage:

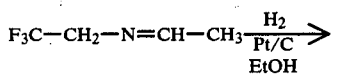

F$_3$C—CH$_2$—NH—CH$_2$—CH$_3$

2nd stage:

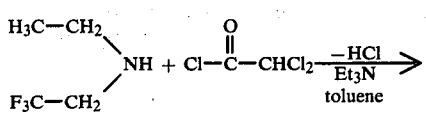

The fluorinated halogenoacetamides of the formula (IV) are suitable for improving the tolerance of crop plants to certain herbicidally active thiolcarbamates and acetanilides. They can preferably be employed as antidotes against thiolcarbamates of the general formula

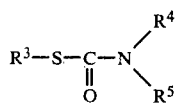  (VII)

in which
R³ represents lower alkyl, benzyl, chlorobenzyl or alkoxybenzyl and
R⁴ and R⁵ independently of one another represent alkyl with 2 to 4 carbon atoms or cyclohexyl, or
R⁴ and R⁵, together with the adjacent nitrogen atom, represent a five-membered to seven-membered heterocyclic ring, or against acetanilides of the general formula

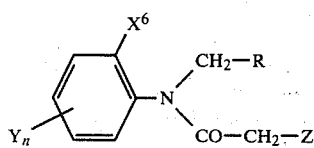  (VIII)

in which
R represents an optionally substituted azole radical bonded via N,
X⁶ and Y are identical or different and represent alkyl,
Z represents halogen and
n represents 0, 1 or 2,
or of the formulae

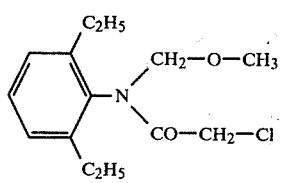  (IX)

or

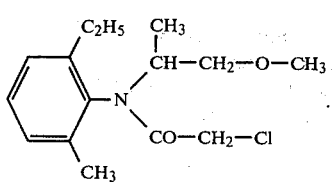  (X)

The good antagonistic action of the fluorinated halogenoacetamides of the formula (IV) can be seen from the following example.

In this example, the substances shown below are used as test compounds (antidote or herbicide):

(A)=

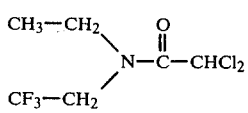

(dichloroacetic acid N-(2,2,2-trifluoroethyl)-N-ethylamide)

(B)=

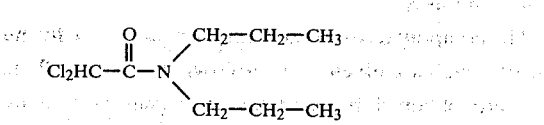

(N,N-di-n-propyl-dichloroacetamide)

(C)=

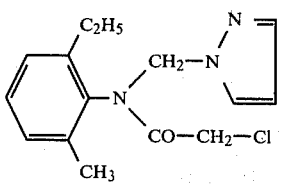

(2-methyl-6-ethyl-N-(pyrazol-1-yl-methyl)-chloroacetanilide).

EXAMPLE A

Pre-emergence test

Solvent: 5 parts by weight of acetone
Emulsifier: 1 part by weight of alkylaryl polyglycol ether To produce a suitable preparation of active compound, 1 part by weight of herbicidal active compound or antidote, or of a mixture of antidote and herbicidal active compound, was mixed with the stated amount of solvent, the stated amount of emulsifier was added and the concentrate was diluted with water to the desired concentration.

Seeds of the test plants were sown in normal soil and, after 24 hours watered with the herbicide preparation or antidote preparation or with the preparation of antidote and herbicidal active compound. It was expedient to keep constant the amount of water per unit area. The concentration of the active compound in the preparation was of no importance, only the amount of active compound applied per unit area being decisive. After three weeks, the degree of damage to the plants was rated in % damage in comparison to the development of the untreated control. The figures denoted:

0% no action (like untreated control)
100% total destruction

Evaluation of the test results shows that the fluorinated halogenoacetamide (A) is more suitable for increasing the tolerance of crop plants to the herbicide (C) than is the comparison compound (B).

PREPARATIVE EXAMPLES

Example 1

$$CF_3-CH_2-N=CH-CH_3 \qquad (1)$$

44 g (1 mol) of freshly distilled acetaldehyde were added dropwise to 99 g (1 mol) of 2,2,2-trifluoroethylamine in the course of 60 minutes, while cooling with ice. The mixture was subsequently stirred for 1 hour, 15 g of solid potassium hydroxide were added and the phases were separated. The organic phase was dried over about 5 g of solid potassium hydroxide and then distilled over a short column. After first runnings (20 g; boiling point: 18°–42° C.) consisting of unreacted amine and acetaldehyde, 77.5 g (62% of theory) of ethylidene-2,2,2-trifluoroethylamine were obtained.

Boiling point=73°–74° C.

$n_D^{20} = 1.3415$.

The compounds of the general formula (I), the formulae of which are given in the following Examples 2 and 3, were obtained by methods analogous to that described in Example 1.

Example 2

  (2)

Yield: 64% of theory.
Boiling point = 93°–95° C.

Example 3

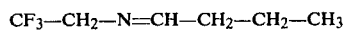  (3)

Yield: 72% of theory.
Boiling point = 116°–118° C.

Example IV-1

Preparation of dichloroacetic acid N-(2,2,2-trifluoromethyl)-N-ethyl-amide (a)

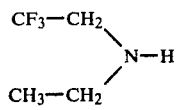

125 g (1 mol) of ethylidene-2,2,2-trifluoroethylamine were dissolved in 250 ml of absolute ethanol, 4 g of platinum-on-charcoal (5% strength) were added and hydrogenation was carried out under a hydrogen pressure of 10 bars at 30° C. for 90 minutes. After filtering off the catalyst, the filtrate was acidified with concentrated hydrochloric acid and concentrated to dryness under reduced pressure. 100 ml of 50% strength aqueous sodium hydroxide solution were added to the product thereby obtained and the mixture was distilled. 83 g (65% of theory) of 2,2,2-trifluoroethyl-N-ethylamine were obtained in this manner.

Boiling point = 61°–62° C.
$n_D^{20} = 1.3335$.

(b)

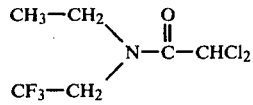

A solution of 14.7 g (0.1 mol) of dichloroacetyl chloride in 20 ml of toluene was a added dropwise to a solution of 12.7 g (0.1 mol) of 2,2,2-trifluoroethyl-N-ethylamine and 10.1 g (0.1 mol) of triethylamine in 50 ml of toluene, while cooling with ice. During this addition, the temperature of the reaction mixture was allowed to rise to 30° C. The mixture was subsequently stirred for 30 minutes, the solid which had precipitated was filtered off and the filtrate was concentrated under reduced pressure.

23.8 g (quantitative yield) of dichloroacetic acid N-(2,2,2-trifluoroethyl)-N-ethylamide with a refractive index $n_D^{20}$ of 1.4472 were obtained in this manner.

It will be understood that the specification and examples are illustrative but not limitative of the present invention and that other embodiments within the spirit and scope of the invention will suggest themselves to those skilled in the art.

What is claimed is:

1. Fluorinated azomethine compound of the formula

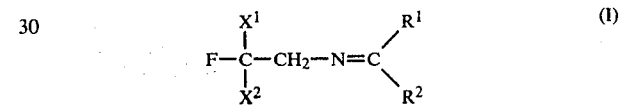 (I)

wherein

X¹ is hydrogen, fluorine or chlorine;
X² is hydrogen, fluorine or chlorine;
R¹ is hydrogen methyl, ethyl, n-propyl or n-butyl and
R² is hydrogen, methyl or ethyl.

2. Compound as claimed in claim 1 wherein X¹ is hydrogen.

3. Compound as claimed in claim 1 wherein X¹ is fluorine or chlorine.

4. Compound as claimed in claim 1 wherein R¹ is hydrogen.

5. Fluorinated azomethine compound as claimed in claim 1 designated ethylidene-2,2,2-trifluoroethylamine.

6. Fluorinated azomethine compound as claimed in claim 1 designated propylidene-2,2,2-trifluoroethylamine.

7. Fluorinated azomethine compound as claimed in claim 1 designated butylidene-2,2,2-trifluoroethylamine.

* * * * *